US009528256B2

(12) United States Patent
Yang et al.

(10) Patent No.: US 9,528,256 B2
(45) Date of Patent: Dec. 27, 2016

(54) FLOW CHANNEL SWITCHING APPARATUS FOR BIDET NOZZLE

(71) Applicant: NANUTECH Co., Ltd., Gimpo-si (KR)

(72) Inventors: Sang Il Yang, Seongnam-si (KR); Man Ju Jung, Incheon (KR); Min Soo Kim, Gimpo-si (KR); Hak Kyu Kim, Seoul (KR); Young Hoon Yoo, Seoul (KR)

(73) Assignee: NANUTECH CO., LTD., Gimpo-Si (KR)

( * ) Notice: Subject to any disclaimer, the term of this patent is extended or adjusted under 35 U.S.C. 154(b) by 0 days.

(21) Appl. No.: 14/842,579

(22) Filed: Sep. 1, 2015

(65) Prior Publication Data
US 2016/0090725 A1    Mar. 31, 2016

(30) Foreign Application Priority Data

Sep. 26, 2014  (KR) .................. 10-2014-0129093

(51) Int. Cl.
   *A61H 35/00*      (2006.01)
   *E03D 9/08*       (2006.01)
   *A61M 3/06*       (2006.01)
(52) U.S. Cl.
   CPC . *E03D 9/08* (2013.01); *A61M 3/06* (2013.01)
(58) Field of Classification Search
   USPC ...................................... 4/443–448
   See application file for complete search history.

(56) References Cited

U.S. PATENT DOCUMENTS

| 7,096,518 B2 * | 8/2006 | Takenaga .................. E03D 9/08 4/420.2 |
| 2011/0203044 A1 * | 8/2011 | Lim .......................... E03D 9/08 4/447 |

FOREIGN PATENT DOCUMENTS

| JP | 2011-042981 | 3/2011 |
| KR | 20-0401806 | 11/2005 |
| KR | 10-0832506 | 5/2008 |
| KR | 20-2009-0000750 | 1/2009 |

OTHER PUBLICATIONS

English Translation of Abstract of 2011-042981.
(Continued)

*Primary Examiner* — Lauren Crane
(74) *Attorney, Agent, or Firm* — KORUS Patent, LLC; Seong Il Jeong (57) ABSTRACT

The present invention relates a flow channel switching apparatus for bidet nozzle which is capable of providing a rectal injection function in addition to anus and genitalia cleaning, which makes the bowel movement comfortable; of fluidly connecting the water tank and the drain hole to drain cold water supplied to prevent the water tank from overheating during initial stage of providing hot water and the final stage of the cleaning, even in a state where the water is not supplied to the anus cleaning hole, the genitalia cleaning hole, or the rectal injection hole, which allows reliable use of the bidet; and when the rotating plate is rotated to fluidly connect the supply through hole of the rotating plate and the anus cleaning hole, the genitalia cleaning hole, or the rectal injection hole penetrated through the disc valve, the supply through hole is fluidly connected to the respective supply hole to supply water, or either one of the first and the second drain through hole is fluidly connected to the discharge hole to guide water to be drained, which allows reliable use of bidet.

7 Claims, 9 Drawing Sheets

(56) References Cited

OTHER PUBLICATIONS

English Translation of 20-0401806.
English Translation of 10-0832506.
English Translation of 20-2009-0000750.

* cited by examiner

FLOW CHANNEL SWITCHING APPARATUS FOR BIDET NOZZLE

CROSS-REFERENCE TO RELATED APPLICATION(S)

This application claims the benefit of Korean Patent Application No. 10-2014-0129093, filed on Sep. 26, 2014, which is hereby incorporated by reference herein in its entirety.

BACKGROUND

1. Technical Field

The present invention relates to a bidet and is more particularly concerned with a flow channel switching apparatus for bidet nozzle which is capable of providing a rectal injection function in addition to anus and genitalia cleaning, which makes the bowel movement comfortable; of fluidly connecting the water tank and the drain hole to drain cold water supplied to prevent the water tank from overheating during initial stage of providing hot water and the final stage of the cleaning, even in a state where the water is not supplied to the anus cleaning hole, the genitalia cleaning hole, or the rectal injection hole, which allows reliable use of the bidet and when the rotating plate is rotated to fluidly connect the supply through hole of the rotating plate and the anus cleaning hole, the genitalia cleaning hole, or the rectal injection hole penetrated through the disc valve, the supply through hole is fluidly connected to the respective supply hole to supply water, or either one of the first and the second drain through hole is fluidly connected to the discharge hole to guide water to be drained, which allows reliable use of bidet.

2. Description of the Related Art

In general, a bidet is an apparatus which, after using the toilet, washes the anus or genitalia with water sprayed from the sprayer nozzle by a button operation of the user, and is widely used in households or office buildings.

The water sprayed from the sprayer nozzle can be sprayed to the anus or genitalia through the valve apparatus for flow channel switching for bidet disclosed in Korean Patent No. 10-0785514 to wash the anus or genitalia.

According to Korean Patent No. 10-0785514, while a rotating plate coupled to a drive shaft is rotated by the power of the drive motor, water is supplied to the first and second holes of the main discharge port, which is fluidly connected thereto, thereby washing the anus or genitalia, and then draining the water through the sub-discharge port.

However, the structure having two discharge ports for anus cleaning and genitalia cleaning does not have a power injection port for rectal injection. Also, and the structure of the flow channel switching part is complicated, thus making the productivity low and the manufacturing costs high, which is economically disadvantageous.

SUMMARY

The present invention has been made keeping in mind the above problems encountered in the prior arts, and an object of the present invention is to provide to flow channel switching apparatus for bidet nozzle which is capable of providing a rectal injection function in addition to anus and genitalia cleaning, which makes the bowel movement comfortable; and of fluidly connecting the water tank and the drain hole to drain cold water supplied to prevent the water tank from overheating during initial stage of providing hot water and the final stage of the cleaning, even in a state where the water is not supplied to the anus cleaning hole, the genitalia cleaning hole, or the rectal injection hole, which allows reliable use of the bidet.

Another object of the present invention is to provide a flow channel switching apparatus for bidet nozzle in which, when the rotating plate is rotated to fluidly connect the supply through hole of the rotating plate and the anus cleaning hole, the genitalia cleaning hole, or the rectal injection hole penetrated through the disc valve, the supply through hole is fluidly connected to the respective supply hole to supply water, or either one of the first and the second drain through hole is fluidly connected to the discharge hole to guide water to be drained, which allows reliable use of bidet, and further which can increase productability and economic efficiency by simplification of the guide structure of water drainage.

A flow channel switching apparatus for bidet nozzle according to the present invention comprises:

a rotating shaft coupled to a drive shaft of a drive motor to rotate in forward and backward directions;

a housing mounted on the drive motor while accommodating the mating shaft to be protruded into the interior, a rotating plate rotatably coupled to the rotating shaft protruded into the housing, and rotated by the power of the drive motor so as to fluidly connect a supply through hole with respective supply holes of a disc valve to thereby guide water to be supplied by a nozzle and to guide water of a water tank supplied by a malfunction during standby in which respective supply holes of the disc valve are not fluidly connected to the supply through hole to be divined through a discharge hole;

an elastic member mounted between the rotating plate and the rotating shaft to make the rotating plate adhere closely to a disc valve;

a disc valve mounted on the housing to be closely adhered to the rotating plate, wherein the valve having a bidet supply hole, an anus supply hole, an enema supply hole, and a discharge hole pass through to guide movement of water to the nozzle; and nozzle configured such that the bidet supply hole, the anus supply hole, the enema supply hole, and the discharge hole of the disc valve to a genitalia cleaning hole, an anus cleaning hole, a rectal injection hole, and a drain hole are fluidly connected while closely adhered to the housing by accommodating the disc valve.

According to the present invention, the flow channel switching apparatus for bidet nozzle which is capable of providing a rectal injection function in addition to anus and genitalia cleaning, which makes the bowel movement comfortable, are provided. Further, the present apparatus can allow proper draining of water from the water tank even in case in which malfunction such as overheating of the water tank is occurred by fluidly connecting the water tank with the drain hole in a state where water is not supplied to the genitalia cleaning hole, which allows reliable use of the bidet.

Further, according to the present invention, there is an advantage that, when the rotating plate is rotated to fluidly connect the supply hole of the rotating plate with a genitalia cleaning hole, an anus cleaning hole, and a rectal injection hole which passed through the disc valve, the supply through hole is fluidly connected With the respective supply holes to supply water to the supply holes, or a discharge hole is fluidly connected with either one of the first and the second drain through holes to guide drainage of water, which allows reliable use of the bidet. In addition, productivity and economic efficiency can be increased by simplification of the guide structure of water drainage.

BRIEF DESCRIPTION OF THE DRAWINGS

The above and other objects, features and advantages of the present invention will be more clearly understood from the following detailed description taken in conjunction with the accompanying drawings, in which.

DETAILED DESCRIPTION

Hereinafter, the configuration and operation of preferred embodiments of the present invention will be described in detail with reference to the accompanying drawings.

Figure 1:
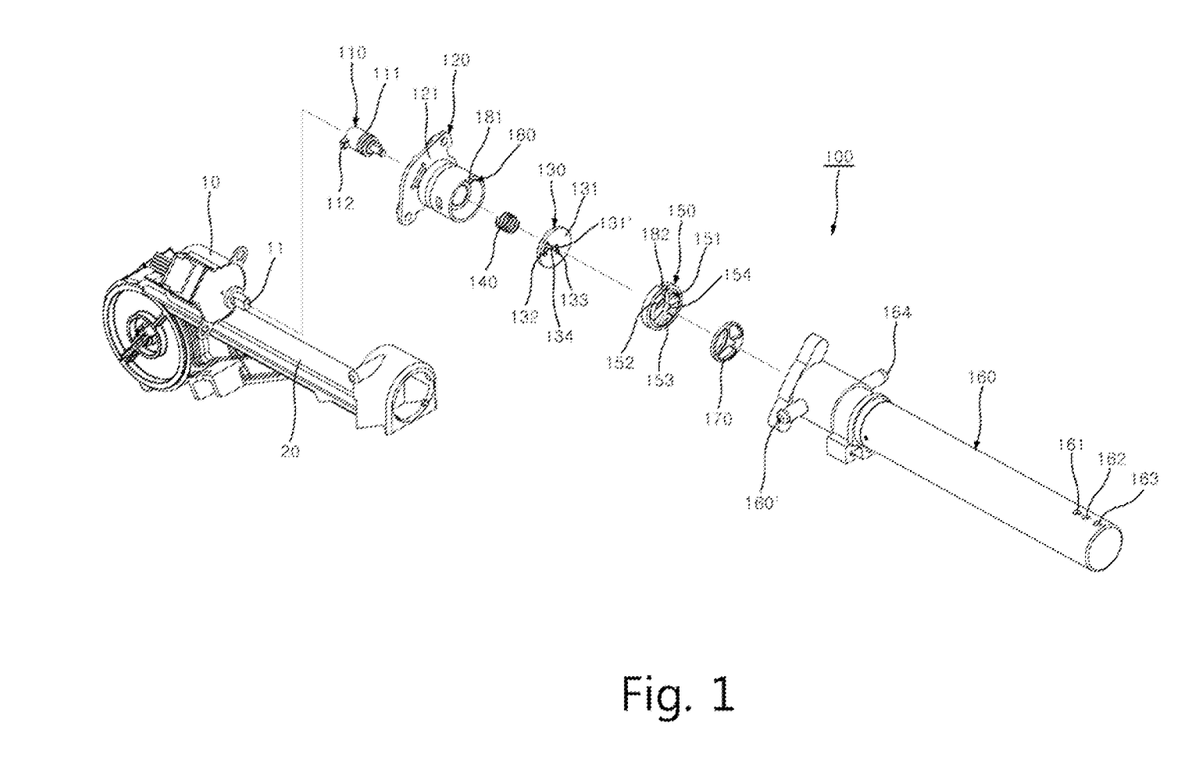
FIG. 1 is a separated perspective view of the bidet according to the present Invention.
Figure 2:
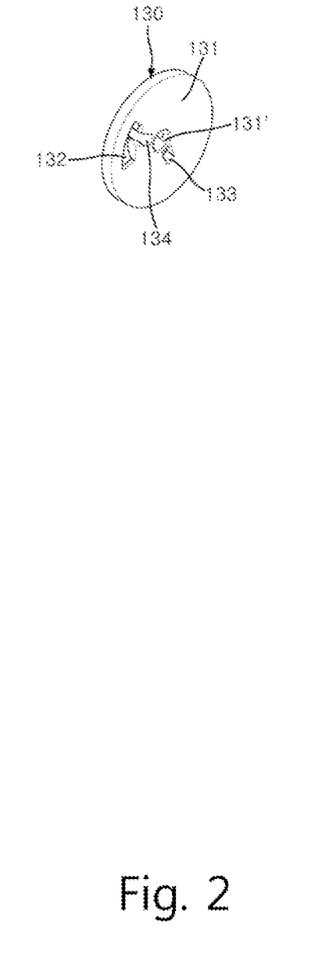
FIG. 2 is a magnified perspective view of the rotating plate of the bidet according to the present invention.
Figure 3:
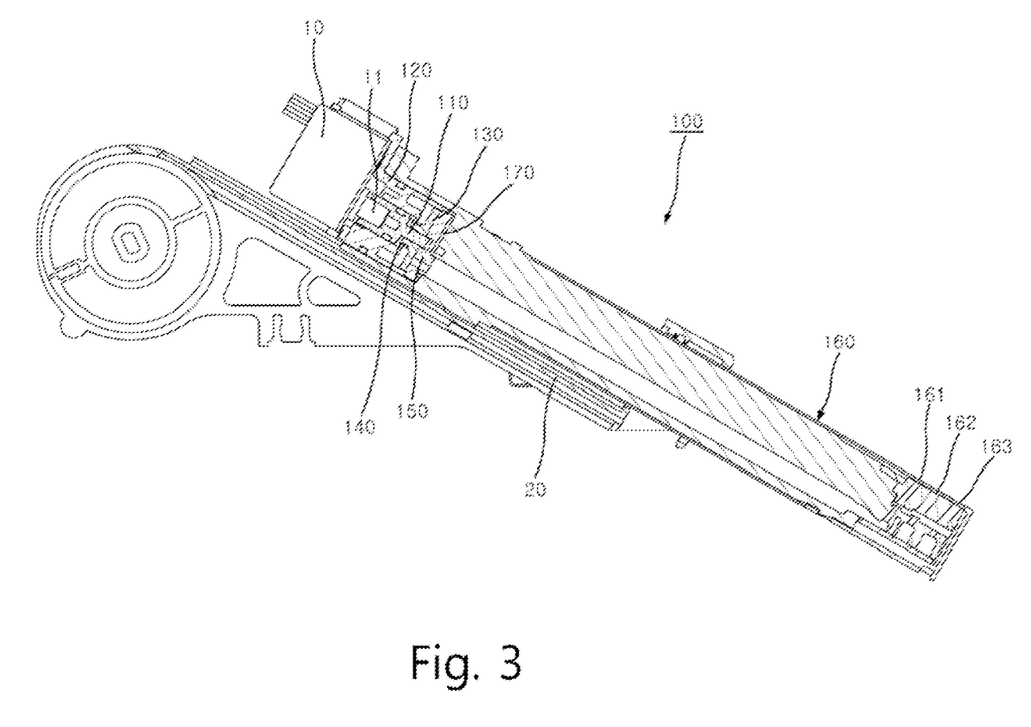
FIGS. 3 and 4 are sectional views of the bidet according to the present invention.
Figure 4:
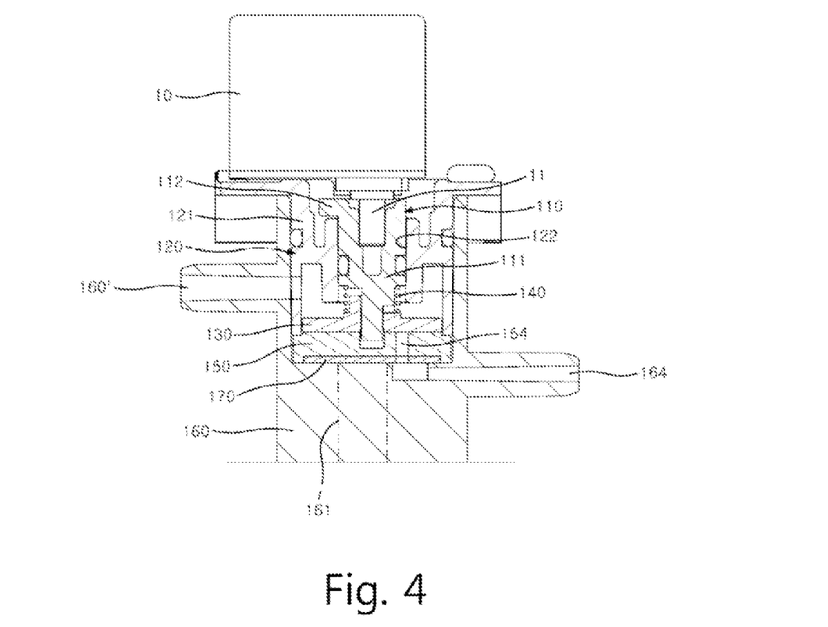

FIG. 1 is a separated perspective view of the bidet according to the present invention. FIG. 2 is a magnified perspective view of the rotating plate of the bidet according to the present invention. FIGS. 3 and 4 are sectional views of the bidet according to the present invention.

A flow channel switching apparatus 100 for bidet nozzle according to the present invention includes: a rotating shaft 110 coupled to a drive shaft 11 of a drive motor 10 to rotate in forward and backward directions; a housing 120 mounted on the drive motor 10 while accommodating the rotating shaft 110 to be protruded into the interior; a rotating plate 130 rotatably coupled to the rotating shaft 110 protruded into the housing 120, and rotated by the power of the drive motor 10 so as to fluidly connect a supply through hole 132 with respective supply holes 151, 152, and 153 of a disc valve 150 to thereby guide water to be supplied to a nozzle 160 and to guide water of a water tank supplied by a malfunction during standby in which respective supply holes 151, 152, and 153 of the disc valve 150 are not fluidly connected to the supply through hole 132 to be drained through a discharge hole 154; an elastic member 140 mounted between the rotating plate 130 and the rotating shaft 110 to make the rotating plate 130 adhere closely to the disc valve 150; a disc valve 150 mounted on the housing 120 to be closely adhered to the rotating plate 130, wherein the valve having a bidet supply hole 151, an anus supply hole 152, an enema supply hole 153, and the discharge hole 154 pass through to guide movement of water to the nozzle 160; and a node 160 closely adhered to the housing 120 to accommodate the disc valve 150 to fluidly connect the bidet supply hole 151, the anus supply hole 152, the enema supply hole 153, and the discharge hole 154 of the disc valve 150 to a genitalia cleaning hole 161, an anus cleaning hole 162, a rectal injection hole 163, and a drain hole 164, which will be later described in more detail.

The rotating shaft 110 includes a rotating body 111 and a rotation control protrusion 112 protruded on one end of the rotating body 111 to control the rotation angle of the rotating shaft 110.

The housing 120 includes: a body 121, inside of which is passed through so that the rotating shaft 110 is protruded into the inside; a rotation space 122 to allow rotation while the rotation control protrusion 112 of the rotating shaft 110 is coupled to one end of the body 121; and an obstructing protrusion 123 to control rotation by obstructing the rotation control protrusion 112 inside the rotation space 122, The rotating plate 130 includes: a rotating plate body 131 through which a coupling hole 131' to couple the rotating, shaft 110 passes; a supply through hole 132 passing through one side of the rotating plate body 131 to be fluidly connected to respective supply holes of the disc valve 150, selectively, so as to guide water supply; a first drain through hole 133 which passing through the rotating plate body 131 apart from the supply through hole 132 by a certain angle to guide drainage of water; and a second drain through hole 134 passing through the rotating plate body 131 to be fluidly connected to the supply through hole 132 to guide drainage of water.

The flow channel switching apparatus for bidet nozzle further includes a disc packing 170 mounted between the disc valve 150 and the nozzle 160 to guide movement of water.

The flow channel switching apparatus for bidet nozzle further includes a rotation prevention unit 180 to prevent rotation of the disc valve 150, and the rotation prevention unit 180 includes a rotation prevention protrusion 181 protruding on an end of either one of the housing 120 and the disc valve 150 and a rotation prevention groove 182 formed in an end of the other one of the housing 120 and the disc valve 150 to fit with the rotation prevention protrusion 181.

Now, installation and operational processes of the present invention having the above described configuration will be described.

First, the rotating shaft 110 is coupled inside of the body 121, inside of which is passed through, of the housing 120 to locate the rotation control protrusion 112 of the rotating shaft 110 in the rotation space 122 in the housing 120. Then, the coupling hole 131' passes through the rotating Plate body 131 of the rotating body 130 to the rotating shaft 110 which is coupled inside of the body 121 of the housing 120. There is the elastic member 140 between the rotating plate 130 and the rotating shaft 110 to make the rotating plate 130 adhere closely to the disc valve 150, which will be described later.

At this time, the coupling hole 131 ' of the rotating plate 130 and the rotating shaft 110 coupled to the coupling hole 131' may have the same polygon shape to rotate the rotating plate 130 in accordance with the rotation of the rotating shaft 110. Alternatively, a protrusion (not shown) on either one of the rotating shaft 110 and the coupling hole 131' and a groove (not shown) on the other one of the rotating shaft 110 and the coupling hole 131' may be formed to rotate the rotating plate 130 in accordance with the rotation of the rotating shaft 110 by the coupling of the protrusion and the groove.

Once the rotating plate 130 is coupled to the rotating shaft 110, the disc valve 150 coupled with the disc packing is adhered closely to the body 121 of the housing 120 to fluidly connect the respective supply holes to the corresponding holes in the nozzle 160. Also, the rotation prevention unit 181 of the rotation prevention unit 180 protruding on one end of either one of the housing 120 and the disc valve 150 may be coupled to the rotation prevention groove 182 formed in one end of the other one of the housing 120 and the disc valve 150 to prevent rotation of the disc valve 150.

Further, the nozzle 160 is fixed closely to the housing 20 so that the bidet supply hole 151, the anus supply hole 152, and the enema supply hole 153 of the disc valve 150 are fluidly connected to the genitalia cleaning hole 161, the anus cleaning hole 162, and the rectal infection hole 163, which finishes the installation of the flow channel switching apparatus 100. Then, the nozzle 160 is fixed to the support 20 having a guide rail and installed to a bidet on which a water tank and various components are mounted according to the design drawing, and the bidet is coupled to the hydrant according to a conventional method.

As a person who sat on a bidet seat installed according to the above described process presses an anterior cleaning, posterior cleaning, or enema button after or dining a use of the toilet, the flow channel switching apparatus 100 moves forward along the guide rail of the support 20 and appears out of the bidet, and, at the same time, water stored in the water tank is supplied to an inlet hole 160' of the nozzle 160.

Figure 5:
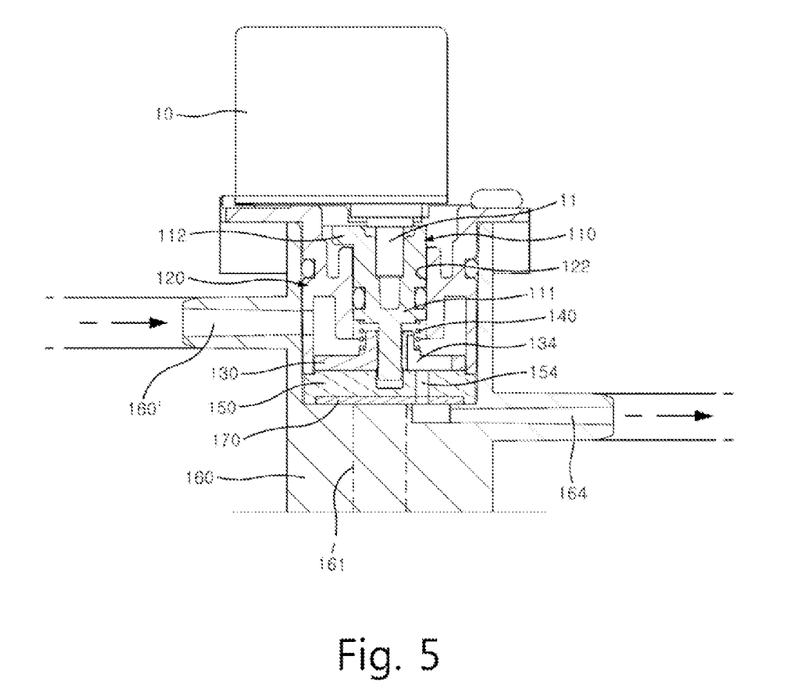
FIGS. 5, 6, 7, 8, 9, 10, 11, and 12 are diagrams showing the operational states of the bidet according to the present invention.
Figure 6:
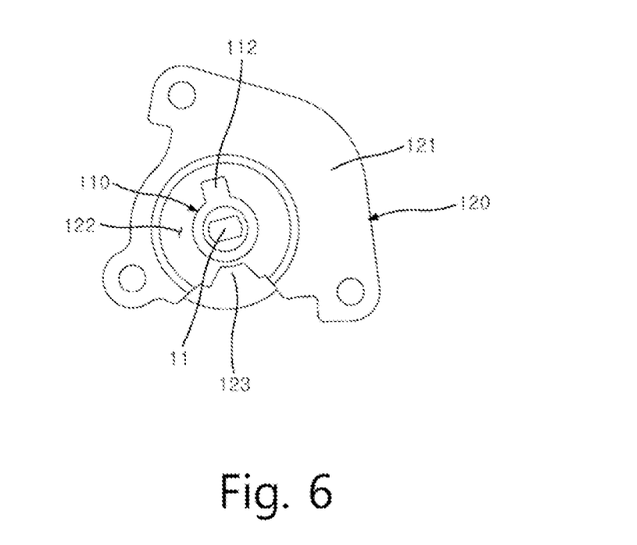
Figure 7:
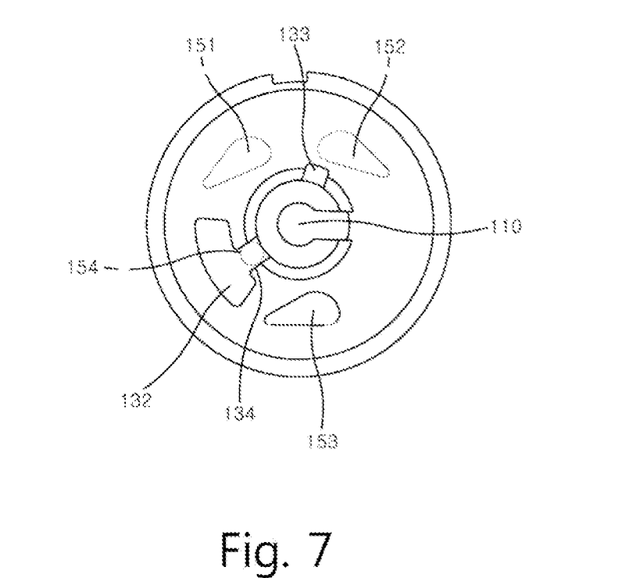

The water supplied to the inlet hole 160', as shown in FIGS. 5 to 7, is drained via the second drain through hole 134 of the rotating plate 130 and the drain hole 164 of the nozzle 160 until the rotating plate 130 rotates in forward or backward directions in accordance with the pressed button so that the supply through hole 132 of the rotating plate 130 is fluidly connected to the supply hole corresponding to the respective button. It is to drain the water in the water tank of hot water to self wash the nozzle 160 or to drain the overheated hot water of the heating tank which heats water from the hydrant instantly.

Figure 8:
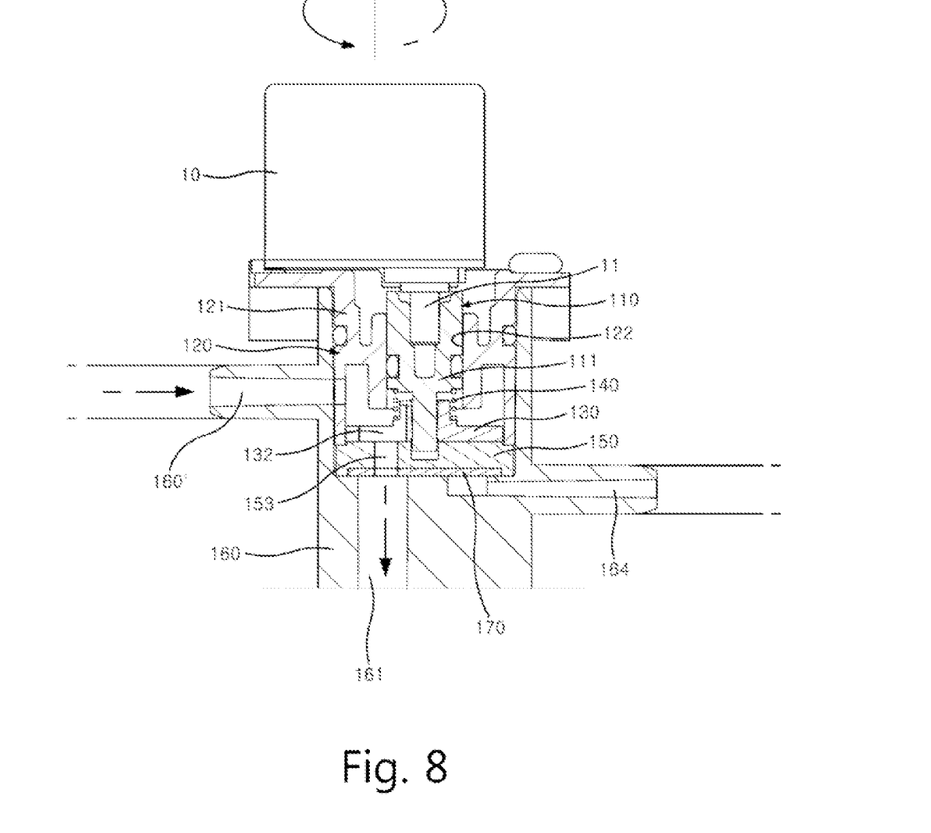
Figure 9:
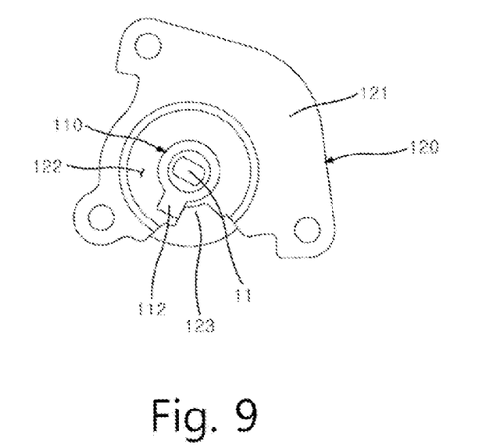
Figure 10:
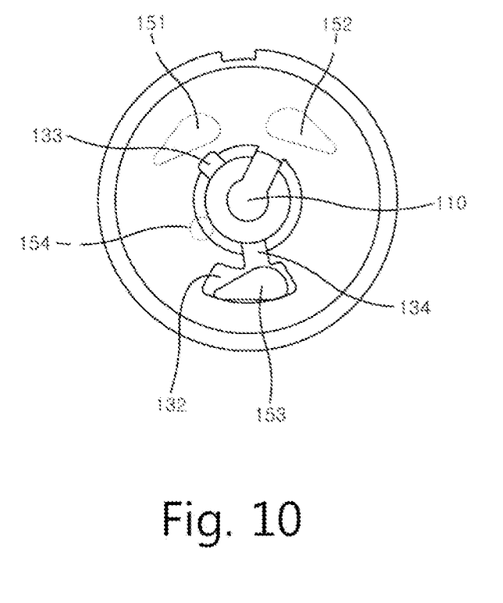

While the water is drained through the drain hole 164 via the second drain through hole 134 in accordance with the control of a control unit, as shown in FIGS. 8 to 10, the rotating shaft 110 and the drive shaft 11 of the drive motor 10 rotate in forward or backward directions to rotate the rotating plate 130 coupled to the rotating shaft 110, which makes the supply through hole 132 of the rotating plate 130 be fluidly connected to any one of the supply holes in accordance with the pressed button.

Here, rotation angles of the rotating shaft 110 are fixed in accordance with the respective supply holes 151, 152 and 153 of the disc valve 150, which makes the rotation control protrusion 112 of the rotating shaft 110 rotate precisely along the rotation space 122 of the housing 120. Even if the rotating shaft 110 rotates more than the fixed rotation angle due to the malfunction of the drive motor 10, the rotation control protrusion 112 of the rotating shall 110 rotating along the rotation space 122 of the housing 120 is obstructed by the obstructing protrusion 123 to stop the rotation of the rotating shall 110.

Also, as the supply through hole 132 is fluidly connected to the supply hole corresponding to the pressed button in accordance with the rotation of the rotating plate 130, the water supplied through the inlet hole 160' is supplied to the supply hole through the supply through hole 132, and, at the same time, the second drain through hole 134 is separated from the drain hole 164 of the nozzle 160 and closes the drain hole 164 to shut off the water drainage.

Figure 11:
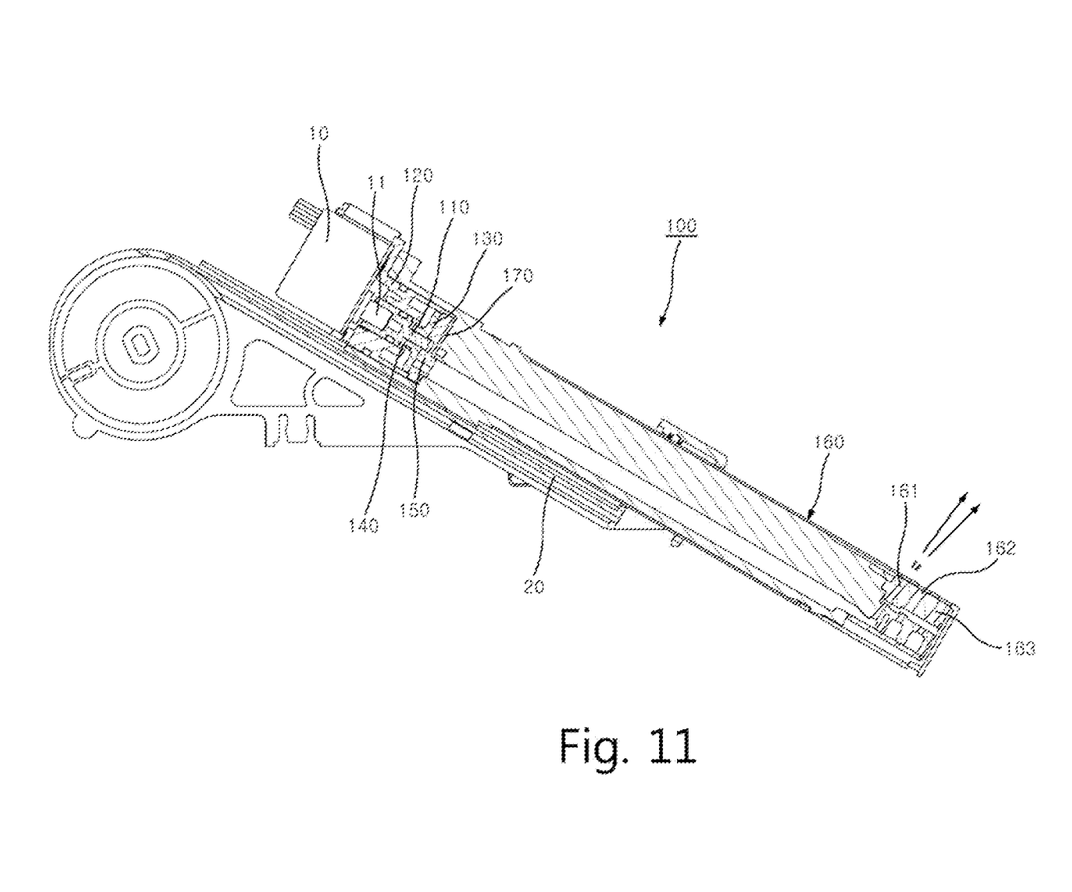

Water supplied to the supply hole through the supply through hole 132, as shown in FIG. 11, is sprayed through one of the genitalia cleaning hole 161, the anus cleaning hole 162, and the rectal injection hole 163, and the water sprayed from the one of the holes is to perform genitalia cleaning, anus cleaning, and rectal injection for the user.

Figure 12:
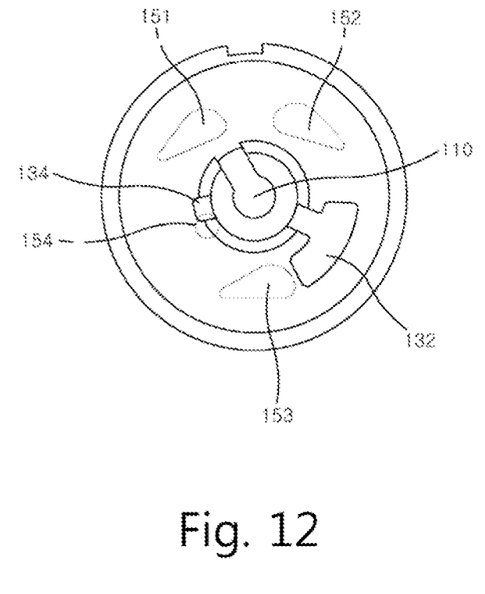

Further, in case that the second drain through hole 134 and the supply through hole 132 are closed by the disc valve 150 as the supply through hole 132 is placed between the supply holes by the rotation of the rotating plate 130 in accordance with the pressing of the anterior cleaning, posterior cleaning, or enema button, as shown in FIG. 12, the first drain through hole 133 is fluidly connected to the discharge hole 154 to drain water supplied through the inlet hole 160'

As the person presses a stop button upon completion of the genitalia cleaning, the anus cleaning, or the rectal injection, under the control of a control unit, water supplied from the water tank through the inlet hole 160' is stopped and simultaneously the flow channel switching apparatus 100 moves backward along the guide rail of the support 20 and enters into the bidet.

Also, as the rotating shaft 110 and the drive shaft 11 of the drive motor 10 rotate in backward or forward directions to restore the original positions, the supply through hole 132 of the rotating plate 130 coupled to the rotating shaft is separated from the supply hole and the rotating plate body 131 closes the supply hole to shut off the water supply. At the same time, the second drain through hole 133 is fluidly connected to the discharge hole 154 and drains the water dropping down from the water tank through the drain hole, and the apparatus waits for the next operation.

Here, the reason why the water is drained through the drain hole 164 after the water is sprayed through the nozzle is to smoothly discharge the water used to cool down the heating tank heated to generate hot water.

Although the specific embodiments of the present invention have been disclosed for illustrative purposes, those skilled in the art will appreciate that various modifications, additions and substitutions are possible without departing from the scope and spirit of the invention as disclosed in the accompanying claims.

What is claimed is:
1. A flow channel switching apparatus for bidet nozzle comprises:
   a rotating shaft coupled to a drive shaft of a drive motor to rotate in forward and backward directions;
   a housing mounted on the drive motor while accommodating the rotating shaft to be protruded into the interior;
   a rotating plate rotatably coupled to the rotating shaft protruded into the housing, and rotated by the power of the drive motor so as to fluidly connect a supply through hole with respective supply holes of a disc valve to thereby guide water to be supplied by a nozzle and to drain water of a water tank supplied by a malfunction during standby in which respective supply holes of the disc valve are not fluidly connected to the supply through hole through a discharge hole;
   an elastic member mounted between the rotating plate and the rotating shaft to make the rotating plate adhere closely to a disc valve;
   a disc valve mounted on the housing to be closely adhered to the rotating plate, wherein the valve having a bidet supply hole, an anus supply hole, an enema supply hole, and the discharge hole pass through to guide movement of water to the nozzle; and
   a nozzle configured such that the bidet supply hole, the anus supply hole, the enema supply hole, and the discharge hole of the disc valve are fluidly connected to a genitalia cleaning hole, an anus cleaning hole, a rectal injection hole, and a drain hole while closely adhered to the housing by accommodating the disc valve.

2. The flow channel switching apparatus for bidet nozzle of claim 1, wherein the rotating shaft comprises:
   a rotating body; and
   a rotation control protrusion radially protruded on an end of the rotating body to control the rotation angle of the rotating shaft.

3. The flow channel switching apparatus for bidet nozzle of claim 1, wherein the housing comprises:
   a body, inside of which is passed through so that the rotating shaft is protruded into the interior;

a rotation space to allow rotation while the rotation control protrusion of the rotating shaft is coupled to one end of the body; and an obstructing protrusion to control rotation by obstructing the rotation control protrusion inside the rotation space.

4. The flow channel switching apparatus for bidet nozzle of claim 1, wherein the rotating plate comprises:

a rotating plate body through which a coupling hole to couple the rotating shaft is passed;

a supply through hole which is passed through one side of the rotating plate body and fluidly connected to respective supply holes of the disc valve selectively to guide water supply;

a first drain through hole passing through the rotating plate body apart from the supply through hole by a certain angle to guide drainage of water; and a second drain through hole passing through the rotating plate body to be fluidly connected to the supply through hole to guide drainage of water.

5. The flow channel switching apparatus for bidet nozzle of claim 1, further comprising a disc packing mounted between the disc valve and the nozzle to guide movement of water.

6. The flow channel switching apparatus for bidet nozzle of claim 1, further comprising a rotation prevention unit to prevent rotation of the disc valve.

7. The flow channel switching apparatus for bidet nozzle of claim 1, wherein the rotation prevention unit comprises:

a rotation prevention protrusion protruding on an end of either one of the housing and the disc valve; and a rotation prevention groove formed in an end of the other one of the housing and the disc valve to fit with the rotation prevention protrusion.

* * * * *